US006312935B1

United States Patent
Kiy et al.

(10) Patent No.: US 6,312,935 B1
(45) Date of Patent: Nov. 6, 2001

(54) CATHEPSIN-L, THE PRE-PROFORM THEREOF AND THE CORRESPONDING PROPEPTIDE FROM CILIATES (75) Inventors: Thomas Kiy, Frankfurt; Joachim Schultz, Ammerbuch, both of (DE)

(73) Assignees: Hoechst Research & Technology; Deutschland GmbH & Co. KG, both of (DE)

( * ) Notice: Subject to any disclaimer, the term of this patent is extended or adjusted under 35 U.S.C. 154(b) by 0 days.

(21) Appl. No.: 08/981,957

(22) PCT Filed: May 9, 1997

(86) PCT No.: PCT/EP97/02388

§ 371 Date: Apr. 13, 1998

§ 102(e) Date: Apr. 13, 1998

(87) PCT Pub. No.: WO97/43425

PCT Pub. Date: Nov. 20, 1997

(30) Foreign Application Priority Data

May 14, 1996 (DE) .............................. 196 19 366

(51) Int. Cl.[7] .............................. C12N 9/50; C12N 15/57; A61K 38/48

(52) U.S. Cl. .................... 435/212; 435/69.1; 435/252.3; 514/2; 536/24.1

(58) Field of Search .......................... 435/212; 536/24.1; 514/2

(56) References Cited

PUBLICATIONS

H. Völkel et al., European Journal of Biochemistry, 238, 198–206 (1996).

A. Fok and R. Paeste, Experimental Cell Research, vol. 139, No. 1, pp. 159–169, May 1982.

E. Kessler and M. Safrin, Journal of Biological Chemistry, vol. 269, No. 36, pp. 22726–22731.

*Primary Examiner*—Ponnathapu Achutamurthy
*Assistant Examiner*—William W. Moore
(74) *Attorney, Agent, or Firm*—Frommer Lawrence & Haug LLP (57) ABSTRACT The invention relates to the isolation of the prepro form of cathepsin L, of its leader sequence, of cathepsin L and of the affiliated propeptide from ciliates, in particular Paramecium, to the use of these peptides and to a process for preparing cathepsin L from ciliates.

10 Claims, 3 Drawing Sheets

```
                                                                                        CATTATTAGCAGTCGGTTTA                    20

ATGATGTTGTTGGGAGCCAGCCTCTACTTGAACAACATAAGAAGTATCTGATGAAATCGATACAGCAAATCTTTATGCAAATTGGAAA                                        110
*M* M  L  L  G  A  S  L  Y  L  N  N  T  Q  E  V  S  D  E  I  D  T  A  N  L  Y  A  N  W  K                                      -79

ATGAAATATAACAGAAGATATACCAACTAAGAACTAAGAGATGAAATGTACAGATACAAGGTTTTCACAGACAACCTTAACTACATCAGAGCTTTC                                 200
 M  K  Y  N  R  R  Y  T  N  Q  R  D  E  M  Y  R  Y  K  V  F  T  D  N  L  N  Y  I  R  A  F                                      -49

TATGAAAGTCCAGAAGAAGCCACATTCACTTTGGAATTGAATCAATTGCTGATATGAGCTAATAAGAATTTGCTTAAACCTATTTGAGC                                        290
 Y  E  S  P  E  E  A  T  F  T  L  E  L  N  Q  F  A  D  M  S  Q  Q  E  F  A  Q  T  Y  L  S                                      -19

CTCAAAGTTCCAAGAACAGCCAAATTCTAACTTCTAATACAAGGGTGCAGAAGTCGATTGGACTGACAATAAGAAG                                                     380
 L  K  V  P  R  T  A  K  L  N  A  A  N  S  N  F  Q  Y  K  G  A  E  V  D  W  T  D  N  K  K                                       11

GTTAAGTATCCAGCTGTTAAGAACTAAGGATCATGCGGTTCATGCTGGGCCTTCTCTGCAGTCGGAGCACTTGAAATCAACACAGACATT                                       470
 V  K  Y  P  A  V  K  N  Q  G  S  C  G  S  C  W  A  F  S  A  V  G  A  L  E  I  N  T  D  I                                       41

GAACTCAACAGAAAAATACGAATTATCTGAATAAGATTTGGTTGACTGCTCAGGACCATATGACAATGATGATGCAATGGTGGATGGATG                                        510
 E  L  N  R  K  Y  E  L  S  E  Q  D  L  V  D  C  S  G  P  Y  D  N  D  G  C  N  G  G  W  M                                       71

GATTCTGCTTTGAATATGTTGCTGACAACGGTTTGGCTGAAGCTAAAGATTATCCATACACTGCTAAAGATGGAACCTGCAAGACCTCA                                        650
 D  S  A  F  E  Y  V  A  D  N  G  L  A  E  A  K  D  Y  P  Y  T  A  K  D  G  T  C  K  T  S                                      101
```

Fig. 2 (Forts.)

```
GTTAAAAGACCATACACTCACGTCCTAAGGATTCAAGGATATTGACTCATGCGATGAATTAGCCTAAACAATCTAAGAAAGAACAGTCGCT  740
 V  K  R  P  Y  T  H  V  Q  G  F  K  D  I  D  S  C  D  E  L  A  Q  T  I  Q  E  R  T  V  A     131

GTTGCCGTCGATGCCAATCCATGGTAATTCTACAGAAGTGGTCCTCTCCAAATGTACTAAAAACTTAAATCACGGAGTCGTCCTTGTT    830
 V  A  V  D  A  N  P  W  Q  F  Y  R  S  G  V  L  S  K  C  T  K  N  L  N  H  G  V  V  L  V     161

GGTGTTTAAGCTGATGGAGCTTGGAAGATTAGAAACTCATGGGAGATCTAGTTGGGGAGAAGCTGGTCACATCAGACTTGCCGGAGGTGAT  920
 G  V  Q  A  D  G  A  W  K  I  R  N  S  W  G  S  S  W  G  E  A  G  H  I  R  L  A  G  G  D     191

ACTTGCGGGTATCTGTGCTGCTCCATCTTTCCCAATTTTAGGATGAAGACTTTGATTATTCATACATCAATTTACAACAATATTAGTTATT 1010
 T  C  G  I  C  A  A  P  S  F  P  I  L  G  ***                                                 205

TTTAAACTTAAGAAAGACTCTTGCTGATGTTATCAGTGAAGGATTGAAAAAAGTAGGCACTCTCTAATTGGGAGGAGGAGCTGCATCAAA  1100
TGCTCCAGCTAAGGCCTAAGCTCCAGCTGCCAAATAAGAGGCACCAAGCCAGTTGAAAAGGCCCCAGAACCCAGAGAAGACGTTGA      1190
CATGGGTGGTTGTTTGACTGATTATACATTTAGTACATTCATATACATATATTAAATATTTTATCATAAAAAAAAAAAAAAAAA        1276
```

CATHEPSIN-L, THE PRE-PROFORM THEREOF AND THE CORRESPONDING PROPEPTIDE FROM CILIATES

This application corresponds to PCT/EP97/02388, filed May 9, 1997, designating the U.S., which claims priority from German Patent Application 19619366.4 filed May 4, 1996. Each of these documents are hereby incorporated herein by reference.

The invention relates to the isolation of the prepro form of cathepsin L, of its leader sequence, of cathepsin L and of the affiliated propeptide from ciliates, in particular Paramecium, to the use of these peptides and to a process for preparing cathepsin L from ciliates.

The finding that propeptides of different proteases can, after they have been liberated by activation of the protease zymogens, act as protease inhibitors is known. For example, once splitting-off has taken place, the propeptide of Pseudomonas aeruginosa elastase attaches to elastase and thereby gives rise to inactivation of the enzyme (Kessler & Safrin, 1994, J. Biol. Chem., 269, 22726). The propeptides of papain and of papaya proteinase IV act selectively as inhibitors of the mature papaya proteases and of the related B and L cathepsins from rat liver (Taylor et al., 1995, Biochem. Soc. Trans., 23, 80). The propeptides of other cathepsins can also act as protease inhibitors. Thus, the synthetically prepared propeptide of human procathepsin D inhibits bovine cathepsin D (Vagner et al., 1993, Collect. Czech. Chem. Commun., 58, 435).

Cathepsin L, a protease, plays an important role in various syndromes. First, this enzyme is probably of crucial importance for the invasiveness of tumors and the formation of metastases (Pike, 1991, Dissertation Abstr. Intern., 53, 4645). This protease can also be involved in the penetration of pathogenic bacteria or parasitic protozoa into the host tissue. Cathepsin L is also involved in the degradation of bone matrix. This enzyme therefore appears to be a rewarding target in connection with the treatment of osteoporosis (Pharma Japan, September 1995, 1468, 23).

Finally, it may be mentioned that cathepsin L is also involved in the development of inflammatory diseases such as arthritis.

The identification of suitable cathepsin L inhibitors could represent an important step in the development of suitable preparations for the therapy of the said diseases. Furthermore, it would be very advantageous to have a suitable source for isolating relatively large quantities of cathepsin L. This is because the enzyme could be employed in screening systems for finding suitable protease inhibitors. Over and above this, it could be employed, for example, in wound ointments, where it could catalyze the degradation of necrotic tissue.

The present invention consequently relates to a cathepsin L prepro form which can be obtained from ciliates, preferably from Paramecium, particularly preferably from Paramecium tetraurelia, and to the DNA sequence encoding such a protein.

The invention furthermore relates to a cathepsin L from ciliates, preferably from Paramecium, particularly preferably from *Paramecium tetraurelia*, and the affiliated DNA sequence, to a process for its preparation from ciliates, and to its use for preparing a pharmaceutical for treating wounds.

The cathepsin L according to the present invention can furthermore be used for identifying suitable inhibitors, for example by means of so-called molecular modeling.

Furthermore, the present invention provides a cathepsin L propeptide, and its DNA sequence, from ciliates, preferably from Paramecium, particularly preferably from *Paramecium tetraurelia*.

The propeptide of the cathepsin L from ciliates is a highly specific inhibitor of this cathepsin L and is consequently suitable for preparing pharmaceuticals for treating inflammatory diseases, metastasizing tumors, bacterial infections, infections with parasitic protozoa, or osteoporosis.

The present invention furthermore provides a presequence, corresponding to the leader sequence or signal sequence of the cathepsin L from ciliates, preferably from Paramecium, particularly preferably from *Paramecium tetraurelia*, which presequence is translated into the corresponding leader sequence or signal sequence when recombinant peptides or proteins are expressed, thereby resulting in the secretion of the recombinantly expressed peptides or proteins from the ciliate cells.

The present invention is clarified below and with the aid of examples.

The present study describes, for the first time, the isolation of two proteases of the cathepsin L subfamily from the ciliate Paramecium (Protista). Sequencing of the cloned cDNA demonstrates that while conformity with previously described cathepsin L forms from Mammalia and Protista is at most 30%, the characteristic cathepsin L motifs are present both in the prepro region and in the actual enzyme. The pro region encodes a segment of 86 amino acids in length which exhibits the typical ERFNIN (SEQ ID No:14) motif. The pro region was expressed in *E. coli*. The isolated propeptide efficiently (in the nanomolar region) inhibited the Paramecium cathepsin L. By contrast, other cysteine proteases, for example papain and mammalian B, G and H cathepsins were not inhibited even at propeptide concentrations of 13 $\mu$M. The propeptide is consequently an effective and specific inhibitor of cathepsin L. Based on these data, it should be possible to develop a potent and highly specific inhibitor for chemotherapeutic use in the treatment of the abovementioned syndromes.

EXAMPLE

Cathepsin L Assay $^{32}$P-Phosphorylase a (approx. $5 \times 10^4$ cpm/min) was used as substrate. A test mixture (30 $\mu$l) contained 10 $\mu$M substrate, 12 mM Tris/HCl (pH 7.0), 50 $\mu$M EDTA, 10 mM 2-mercaptoethanol, 5 mM caffeine and 6.7 $\mu$g of BSA. The reaction was stopped, after incubating at 30° C. for 10 minutes, by adding 200 $\mu$l of trichloroacetic acid (20% w/v). The radioactivity of the non-precipitable peptides was determined in the supernatant following centrifugation. One unit of enzyme activity corresponds to the quantity which liberates 1 $\mu$mol of soluble $^{32}$P-phosphopeptide/min.

Purification of the Cathepsin L

Mass cultures of the ciliate Paramecium tetraurelia were used as the source. Cathepsin L can be obtained both from the cells and, in large quantities, from the culture medium, since the cells also secrete the enzyme.

All the purification steps were carried out at 4° C. The cells were homogenized in 50 mM Tris/HCl (pH 7.0), 5 mM EDTA using a French press. Cell debris were removed by centrifugation (23,000×g, 60 min; 100,000×g, 60 min). The supernatant was loaded onto a DEAE Sepharose® column which was equilibrated with 20 mM Tris/HCl (pH 7.0). About half the protease activity eluted with the flowthrough. The column was washed with 250 mM NaCl. The remaining protease activity was eluted with 450 mM KCl. After that, the active fractions were purified through a Sephacryl® S-100 HR column. The protease eluted at approximately 27 kDa. The pooled active fractions were subsequently loaded onto a mono Q column. Elution was carried out using a linear gradient (60 ml of from 100 to 350 mM NaCl). Two active proteases (30 kDa and 33 kDa) were separated in this step. Purity was examined by means of SDS-PAGE. When using $^{32}$P phosphorylase a as substrate, the pH optimum of the two isozymes was 6.5; the temperature optimum was 56° C. Sulfhydryl protease-specific inhibitors (e.g. cystatin, leupeptin and TLCK) reduced the activity drastically. On the other hand, inhibitors which were specific for serine proteases (aprotinin), metalloproteases (EDTA) and Asp proteases (pepstatin) had no inhibitory effect. The digestion pattern obtained with phosphorylase and BSA indicated that the two proteases were endoproteinase isozymes.

Amino Acid Sequencing

The proteins were blotted out of the SDS gel onto a polyvinylidene difluoride membrane, and the corresponding 30 kDa and 33 kDa bands were cut out. For the sequencing of protein fragments, the proteins were cleaved with BrCN (350 μg{10 μg of protein) prior to the SDS-PAGE. The sequencing was carried out on an Applied Biosystems sequencer. The NH$_2$ terminus of the 30 kDa band is: GAEVDWTDNKKVKYPAVKNQ (SEQ ID No:1), while that of the 33 kDa band is: GAEVDXTXNK (X is unresolved) (SEQ ID No:2). The sequencing of the BrCN fragments also showed that identical enzyme proteins were involved, with the proteins possibly only being processed differently. In this case, the following sequence was determined for both the proteins: DSAFEYVADNGLAEAKDYPYYASD (SEQ ID No:3). Comparison with the EMBL gene bank using the FASTA program did not indicate any correspondence with known proteins as far as the NH$_2$ terminus was concerned; on the other hand, alignment of the internal 24 mer peptide demonstrated unambiguous correspondence with 19 different cysteine proteases.

Amplification and Subcloning of Cathepsin L

Figure 2:
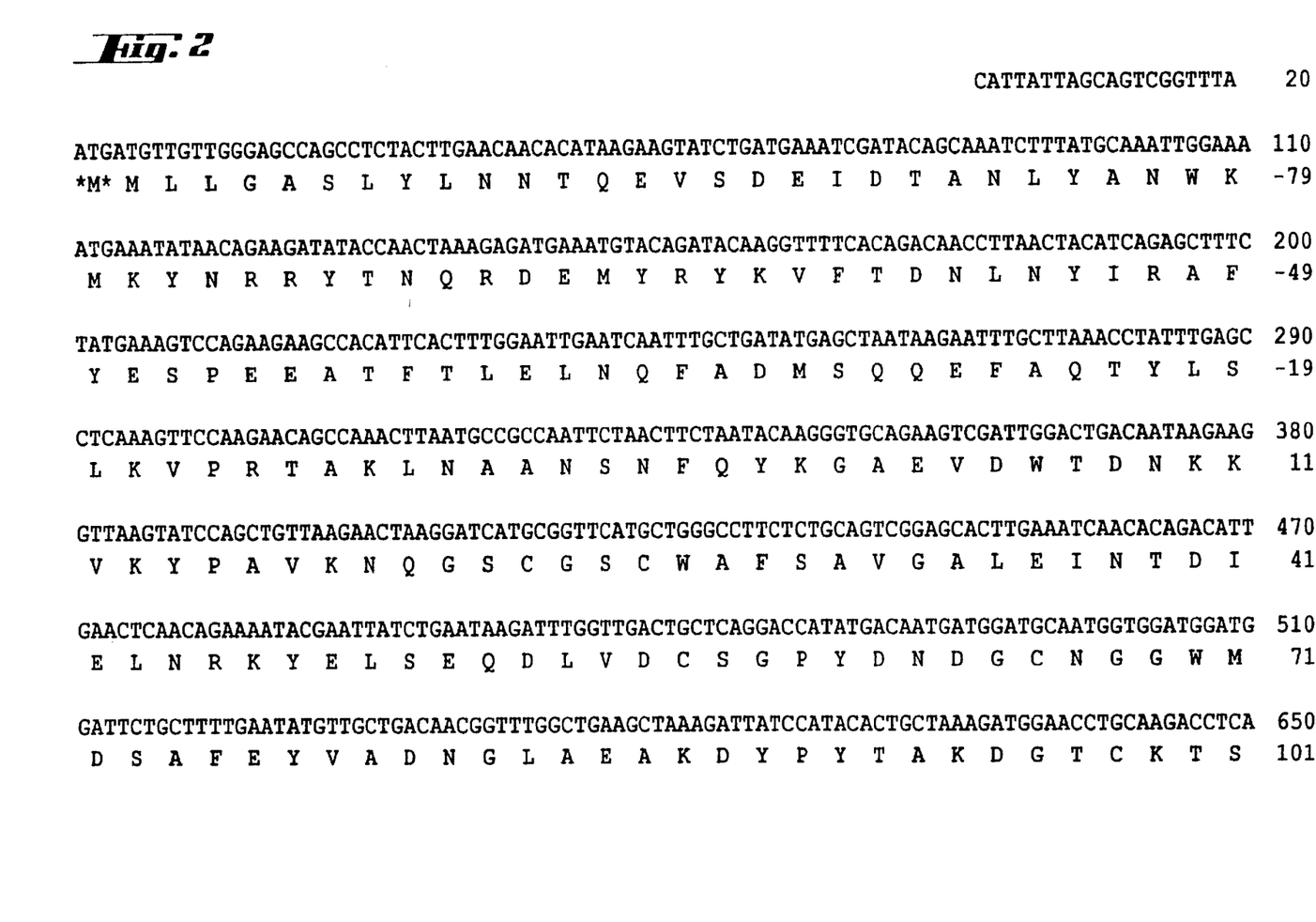
FIG. 2 is a DNA sequence which encodes the prepro form of cathepsin L and the associated amino acid sequence for the protein with 313 amino acids having a molecular weight of 35,031 Da.

Oligonucleotides were prepared on the basis of the amino acid sequencing and taking into account ciliate codon usage. The primers employed were: primer 1 (sense) 5'-GCGGGGTACCGGWGCHGAAGTHGAYTGGACWG-ATAAYAARAARG-3' (SEQ ID No:4), deduced from the NH$_2$-terminal peptide GAEVDWDNKKVK (SEQ ID No:6) and primer 2 (antisense) 5'-TARTANGGRTARTCYTTNGCYTC-3', deduced from the internal peptide sequence EAKDYPYY (SEQ ID No:7). The PCR was carried out in a Perkin-Elmer Thermal Cycler (30 cycles, at 94° C., 55° C. and 72° C. for 1 min in each case). Using these primers, a fragment of 275 bp in length was amplified from a Paramecium cDNA library. Sequencing this DNA fragment provided unambiguous evidence of its similarity to cathepsin L. Thus, the PCR fragment contained the two strongly conserved regions GCNGG (SEQ ID No:8) and CGCSWA (SEQ ID No:9). Two clones having inserts of 1.3 kB were identified in the cDNA library using the 275 bp fragment. Sequencing these clones indicated that they contained identical open reading frames which encoded a protein of 313 amino acids having a calculated molecular weight of 35,031 Da (FIG. 2) (SEQ ID No:12). The deduced amino acid sequence was in agreement with that determined by means of Edman degradation.

The conserved ERFNIN (SEQ ID No:14) motif in the propeptide EX$_2$RX$_2$VFX$_2$NX$_3$IX$_3$N (SEQ ID No:15) and EX$_2$RX$_2$IFX$_2$NX$_3$IX$_3$N (SEQ ID No:16). characterizes the enzyme as H or L cathepsin. Whereas cathepsin H is characterized as an exoprotease, cathepsin L is classified as an efficient endoprotease. The identification as endoproteases of the proteases which are described here suggests that they are in fact forms of cathepsin L. The correspondence of the Paramecium cathepsin L to different mammalian forms is at most 35% (Tab. 1). The correspondence is also only 30% when compared with the Tetrahymena cysteine protease.

TABLE 1

| Cathepsins and proteases as compared with Paramecium cathepsin L | SWISSPROT accession No. | % identity with | |
|---|---|---|---|
| | | mature proteases | pro regions |
| Rat L type | P07154 | 35 | 21 |
| Tetrahymena cysteine protease | L03212 | 30 | 23 |
| Rat H type | P00786 | 30 | 19 |
| Rat S type | Q02765 | 31 | 19 |
| Human B type | P07858 | 21 | 12 | cDNA Library Screening $^{32}$P-labeled PCR fragments were used to screen the cDNA library for corresponding clones. The two clones which were identified in this way were analyzed by Southern blotting. Both the clones encoded an identical peprocathepsin L protease.

Bacterial Expression of the Cathepsin L Propeptide

The cloned gene contains a potential propeptide region from AA-1 to -86. The open reading frame contains five universal TAA stop codons, which encode Q in Paramecium. Before being expressed, they were changed into CAA (encodes Q) by means of site-directed mutagenesis.

The DNA fragment containing the propeptide region was amplified by PCR and introduced, for expression, into the heat-inducible vector pEV41C, which additionally contained a hexa-His tag. The primers which were used for the PCR were 5'-AGGTCGTCATATGAATCTTTATGCAAATTGG (sense) (SEQ ID No:11) and 5'-ATCCTCGAGTCACTTGTATTGGAAGTTAG (antisense) (SEQ ID NO:10). Following transformation, the propeptide was expressed in E. coli strain 2136. Expression was induced by adding LB$_{smp}$ medium which had been preheated to 42° C.

After harvesting, the cells were homogenized and the cell debris was removed by centrifugation. The supernatant was purified on an Ni affinity column (Qiagen). The protein was eluted using 20 mM Tris/HCl (pH 7.5), 8.6% glycerol, 200 mM NaCl and 500 mM imidazole. As expected, a protein having a size of 13.6 kDa was eluted under these conditions.

Figure 1:
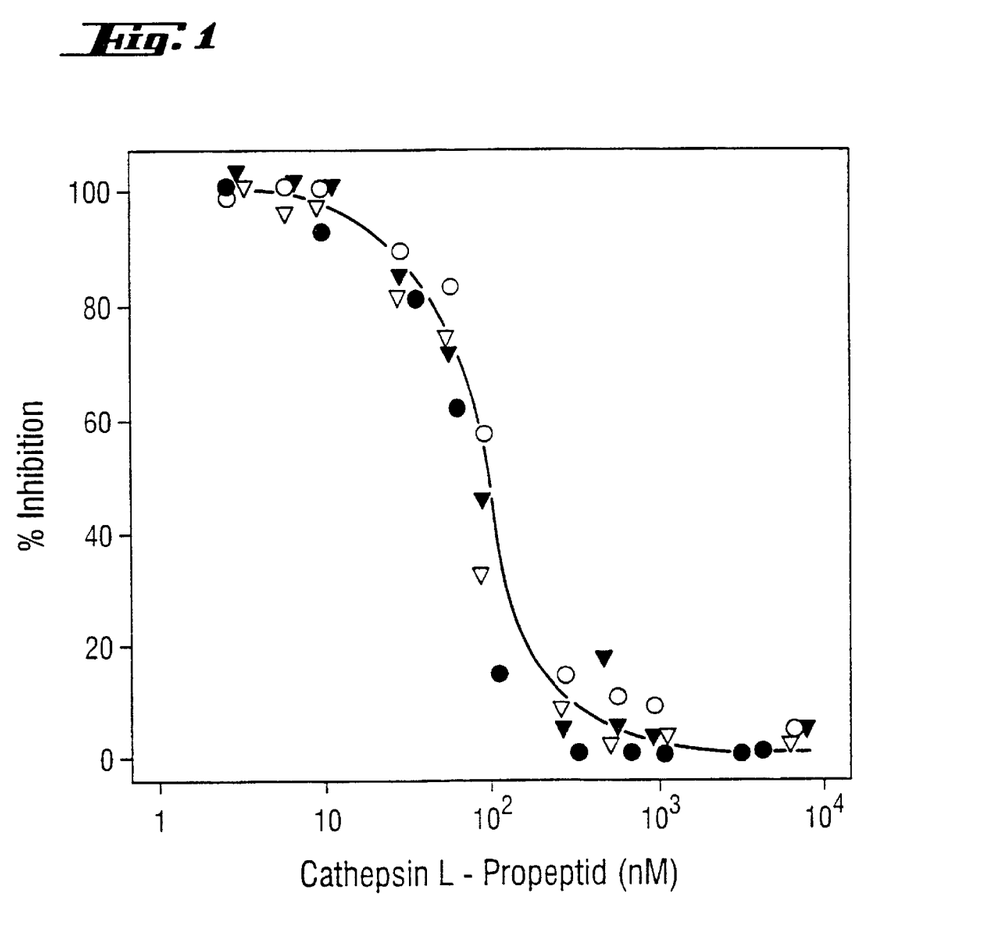
FIG. 1 is a graph depicting the results of inhibition tests comparing the percent inhibition of the 30 kDa cathepsin L isozyme versus the concentration of cathepsin L-propeptide (nM).

In an inhibition test, the propeptide inhibited the 30 kDa cathepsin L isozyme from Paramecium by 50% at a concentration of only 60 nM (FIG. 1). Other proteases (papain, human liver cathepsin H, bovine kidney cathepsin B and leukocyte cathepsin G) were not inhibited even at propeptide concentrations of 13 μM.

What is claimed is:

1. An isolated prepro protein of cathepsin L obtainable from *Paramecium tetraurelia*.

2. The amino acid sequence shown in SEQ ID NO: 13.

3. The amino acid sequence corresponding to amino acids 1 to 22 as shown in SEQ ID NO:13.

4. The propeptide contained in the prepro form of cathepsin L of SEQ. ID NO: 13 as claimed in claim 1.

5. An isolated propeptide of the *Paramecium tetraurelia* cathepsin L having the amino acid sequence shown in SEQ ID NO: 13, corresponding to amino acids from position 23 through position 109.

6. A cathepsin L obtainable from ciliates wherein the ciliate is *Paramecium tetraurelia*.

7. The amino acid sequence corresponding to amino acids 110 to 314 of the amino acid sequence shown in SEQ ID No:13.

8. A pharmaceutical composition comprising a cathepsin L as claimed in claim 6.

9. A wound ointment which comprises cathepsin L as claimed in 6.

10. An isolated nucleic acid sequence comprising the sequence of nucleic adds 1 to 20 of SEQ ID NO: 12.

* * * * *

SEQUENCE LISTING

<160> NUMBER OF SEQ ID NOS: 16

<210> SEQ ID NO 1
<211> LENGTH: 20
<212> TYPE: PRT
<213> ORGANISM: Paramecium tetraurelia

<400> SEQUENCE: 1

Gly Ala Glu Val Asp Trp Thr Asp Asn Lys Lys Val Lys Tyr Pro Ala
 1               5                  10                  15

Val Lys Asn Gln
            20

<210> SEQ ID NO 2
<211> LENGTH: 10
<212> TYPE: PRT
<213> ORGANISM: Paramecium tetraurelia
<220> FEATURE:
<221> NAME/KEY: VARIANT
<222> LOCATION: (1)..(10)
<223> OTHER INFORMATION: Xaa represents any amino acid

<400> SEQUENCE: 2

Gly Ala Glu Val Asp Xaa Thr Xaa Asn Lys
 1               5                  10

<210> SEQ ID NO 3
<211> LENGTH: 24
<212> TYPE: PRT
<213> ORGANISM: Paramecium tetraurelia

<400> SEQUENCE: 3

Asp Ser Ala Phe Glu Tyr Val Ala Asp Asn Gly Leu Ala Glu Ala Lys
 1               5                  10                  15

Asp Tyr Pro Tyr Tyr Ala Ser Asp
            20

<210> SEQ ID NO 4
<211> LENGTH: 36
<212> TYPE: DNA
<213> ORGANISM: Paramecium tetraurelia

<400> SEQUENCE: 4
gcggggtacc gggcgaagtg atggacgata aaaaag                                  36

<210> SEQ ID NO 5
<211> LENGTH: 12
<212> TYPE: PRT
<213> ORGANISM: Paramecium tetraurelia

<400> SEQUENCE: 5

Gly Ala Glu Val Asp Trp Asp Asn Lys Lys Val Lys
 1               5                  10

<210> SEQ ID NO 6
<211> LENGTH: 23
<212> TYPE: PRT
<213> ORGANISM: Paramecium tetraurelia

<400> SEQUENCE: 6

Thr Ala Arg Thr Ala Asn Gly Gly Arg Thr Ala Arg Thr Cys Tyr Thr
 1               5                  10                  15

```
Thr Asn Gly Cys Tyr Thr Cys
            20

<210> SEQ ID NO 7
<211> LENGTH: 8
<212> TYPE: PRT
<213> ORGANISM: Paramecium tetraurelia

<400> SEQUENCE: 7

Glu Ala Lys Asp Tyr Pro Tyr Tyr
 1               5

<210> SEQ ID NO 8
<211> LENGTH: 5
<212> TYPE: PRT
<213> ORGANISM: Paramecium tetraurelia

<400> SEQUENCE: 8

Gly Cys Asn Gly Gly
 1               5

<210> SEQ ID NO 9
<211> LENGTH: 6
<212> TYPE: PRT
<213> ORGANISM: Paramecium tetraurelia

<400> SEQUENCE: 9

Cys Gly Cys Ser Trp Ala
 1               5

<210> SEQ ID NO 10
<211> LENGTH: 31
<212> TYPE: DNA
<213> ORGANISM: Paramecium tetraurelia

<400> SEQUENCE: 10
aggtcgtcat atgaatcttt atgcaaattg g                              31

<210> SEQ ID NO 11
<211> LENGTH: 29
<212> TYPE: DNA
<213> ORGANISM: Paramecium tetraurelia

<400> SEQUENCE: 11
atcctcgagt cacttgtatt ggaagttag                                 29

<210> SEQ ID NO 12
<211> LENGTH: 1276
<212> TYPE: DNA
<213> ORGANISM: Paramecium tetraurelia

<400> SEQUENCE: 12
cattattagc agtcggttta atgatgttgt tgggagccag cctctacttg aacaacacat    60
aagaagtatc tgatgaaatc gatacagcaa atctttatgc aaattggaaa atgaaatata   120
acagaagata taccaactaa agagatgaaa tgtacagata caaggttttc acagacaacc   180
ttaactacat cagagctttc tatgaaagtc cagaagaagc cacattcact ttggaattga   240
atcaatttgc tgatatgagc taataagaat ttgcttaaac ctatttgagc ctcaaagttc   300
caagaacagc caaacttaat gccgccaatt ctaacttcta atacaagggt gcagaagtcg   360
attggactga caataagaag gttaagtatc cagctgttaa gaactaagga tcatgcggtt   420
catgctgggc cttctctgca gtcggagcac ttgaaatcaa cacagacatt gaactcaaca   480
```

-continued

```
gaaaatacga attatctgaa taagatttgg ttgactgctc aggaccatat gacaatgatg      540
gatgcaatgg tggatggatg gattctgctt ttgaatatgt tgctgacaac ggtttggctg      600
aagctaaaga ttatccatac actgctaaag atggaacctg caagacctca gttaaaagac      660
catacactca cgtctaagga ttcaaggata ttgactcatg cgatgaatta gcctaaacaa      720
tctaagaaag aacagtcgct gttgccgtcg atgccaatcc atggtaattc tacagaagtg      780
gtgtcctctc caaatgtact aaaaacttaa atcacggagt cgtccttgtt ggtgtttaag      840
ctgatggagc ttggaagatt agaaactcat ggggatctag ttggggagaa gctggtcaca      900
tcagacttgc cggaggtgat acttgcggta tctgtgctgc tccatctttc ccaattttag      960
gatgaagact ttgattattc atacatcaat ttacaacaat attagttatt tttaaactta     1020
agaaagactc ttgctgatgt tatcagtgaa ggattgaaaa agtaggcac tctctaattg       1080 ggaggaggag ctgcatcaaa tgctccagct aaggcctaag ctccagctgc tgccaaataa     1140
gaggcaccaa agccagttga aaaggcccca gaaccagaag aagacgttga catgggtggt     1200
ttgtttgact gattatacat tttagtacat tcatatacat atattaaata ttttatcata     1260
aaaaaaaaaa aaaaaa                                                      1276
```

<210> SEQ ID NO 13
<211> LENGTH: 314
<212> TYPE: PRT
<213> ORGANISM: Paramecium tetraurelia
<220> FEATURE:
<221> NAME/KEY: PROPEP
<222> LOCATION: (1)..(109)
<223> OTHER INFORMATION: The position numbers for this sequence
      correspond to -108 to 205 of Figure 2.

<400> SEQUENCE: 13

```
Met Met Leu Leu Gly Ala Ser Leu Tyr Leu Asn Asn Thr Gln Glu Val
  1               5                  10                  15

Ser Asp Glu Ile Asp Thr Ala Asn Leu Tyr Ala Asn Trp Lys Met Lys
                 20                  25                  30

Tyr Asn Arg Arg Tyr Thr Asn Gln Arg Asp Glu Met Tyr Arg Tyr Lys
             35                  40                  45

Val Phe Thr Asp Asn Leu Asn Tyr Ile Arg Ala Phe Tyr Glu Ser Pro
         50                  55                  60

Glu Glu Ala Thr Phe Thr Leu Glu Leu Asn Gln Phe Ala Asp Met Ser
 65                  70                  75                  80

Gln Gln Glu Phe Ala Gln Thr Tyr Leu Ser Leu Lys Val Pro Arg Thr
                 85                  90                  95

Ala Lys Leu Asn Ala Ala Asn Ser Asn Phe Gln Tyr Lys Gly Ala Glu
            100                 105                 110

Val Asp Trp Thr Asp Asn Lys Lys Val Lys Tyr Pro Ala Val Lys Asn
        115                 120                 125

Gln Gly Ser Cys Gly Ser Cys Trp Ala Phe Ser Ala Val Gly Ala Leu
    130                 135                 140

Glu Ile Asn Thr Asp Ile Glu Leu Asn Arg Lys Tyr Glu Leu Ser Glu
145                 150                 155                 160

Gln Asp Leu Val Asp Cys Ser Gly Pro Tyr Asp Asn Asp Gly Cys Asn
                165                 170                 175

Gly Gly Trp Met Asp Ser Ala Phe Glu Tyr Val Ala Asp Asn Gly Leu
            180                 185                 190

Ala Glu Ala Lys Asp Tyr Pro Tyr Thr Ala Lys Asp Gly Thr Cys Lys
        195                 200                 205
```

```
Thr Ser Val Lys Arg Pro Tyr Thr His Val Gln Gly Phe Lys Asp Ile
    210             215                 220

Asp Ser Cys Asp Glu Leu Ala Gln Thr Ile Gln Glu Arg Thr Val Ala
225             230                 235                 240

Val Ala Val Asp Ala Asn Pro Trp Gln Phe Tyr Arg Ser Gly Val Leu
            245                 250                 255

Ser Lys Cys Thr Lys Asn Leu Asn His Gly Val Val Leu Val Gly Val
            260                 265                 270

Gln Ala Asp Gly Ala Trp Lys Ile Arg Asn Ser Trp Gly Ser Ser Trp
        275                 280                 285

Gly Glu Ala Gly His Ile Arg Leu Ala Gly Gly Asp Thr Cys Gly Ile
    290             295                 300

Cys Ala Ala Pro Ser Phe Pro Ile Leu Gly
305                 310

<210> SEQ ID NO 14
<211> LENGTH: 6
<212> TYPE: PRT
<213> ORGANISM: Paramecium tetraurelia

<400> SEQUENCE: 14

Glu Arg Phe Asn Ile Asn
  1               5

<210> SEQ ID NO 15
<211> LENGTH: 19
<212> TYPE: PRT
<213> ORGANISM: Paramecium tetraurelia
<220> FEATURE:
<221> NAME/KEY: VARIANT
<222> LOCATION: (1)..(19)
<223> OTHER INFORMATION: Xaa represents any amino acid

<400> SEQUENCE: 15

Glu Xaa Xaa Arg Xaa Xaa Val Phe Xaa Xaa Asn Xaa Xaa Xaa Ile Xaa
  1               5                  10                  15

Xaa Xaa Asn

<210> SEQ ID NO 16
<211> LENGTH: 19
<212> TYPE: PRT
<213> ORGANISM: Paramecium tetraurelia
<220> FEATURE:
<221> NAME/KEY: VARIANT
<222> LOCATION: (1)..(19)
<223> OTHER INFORMATION: Xaa represents any amino acid

<400> SEQUENCE: 16

Glu Xaa Xaa Arg Xaa Xaa Ile Phe Xaa Xaa Asn Xaa Xaa Xaa Ile Xaa
  1               5                  10                  15

Xaa Xaa Asn
```